(12) United States Patent
Thompson et al.

(10) Patent No.: US 9,531,195 B2
(45) Date of Patent: Dec. 27, 2016

(54) INDUCTIVELY RECHARGEABLE IMPLANTABLE DEVICE WITH REDUCED EDDY CURRENTS

(75) Inventors: David L. Thompson, Houston, TX (US); Jianxiang Shen, Houston, TX (US); Anthony W. Cowley, Houston, TX (US); Saadat Hussain, Houston, TX (US); Eric Y. Chow, Houston, TX (US); Jared B. Floyd, Ferndale, WA (US); James L. Flesher, Charlotte, NC (US)

(73) Assignee: CYBERONICS, INC., Houston, TX (US)

( * ) Notice: Subject to any disclaimer, the term of this patent is extended or adjusted under 35 U.S.C. 154(b) by 340 days.

(21) Appl. No.: 13/098,020

(22) Filed: Apr. 29, 2011

(65) Prior Publication Data

US 2012/0274271 A1    Nov. 1, 2012

(51) Int. Cl.
H02J 7/00    (2006.01)
H02J 5/00    (2016.01)
H02J 7/02    (2016.01)

(52) U.S. Cl.
CPC ............... *H02J 5/005* (2013.01); *H02J 7/025* (2013.01)

(58) Field of Classification Search
CPC ........ A61N 1/375; A61N 1/3787; H02J 7/025; A61B 2560/0219
USPC ........................................................ 320/108
See application file for complete search history.

(56) References Cited

U.S. PATENT DOCUMENTS

| 4,014,346 | A |  | 3/1977 | Brownlee et al. |
| 4,665,896 | A |  | 5/1987 | La Forge et al. |
| 5,154,172 | A |  | 10/1992 | Terry, Jr. et al. |
| 5,222,494 | A |  | 6/1993 | Baker, Jr. |
| 5,350,413 | A |  | 9/1994 | Miller |
| 5,411,537 | A |  | 5/1995 | Munshi et al. |
| 5,690,693 | A |  | 11/1997 | Wang et al. |
| 5,702,431 | A |  | 12/1997 | Wang et al. |
| 5,713,939 | A |  | 2/1998 | Nedungadi et al. |
| 5,749,909 | A |  | 5/1998 | Schroeppel et al. |
| 5,913,881 | A | * | 6/1999 | Benz ..................... A61N 1/375 607/36 |
| 5,991,665 | A | * | 11/1999 | Wang et al. .................... 607/61 |

(Continued)

FOREIGN PATENT DOCUMENTS

WO    2011022166 A1    2/2011

OTHER PUBLICATIONS

Yungtaek Jang et al., "A Contactless Electrical Energy Transmission System for Portable-Telephone Battery Chargers," IEEE Transactions on Industrial Electronics, vol. 50, No. 3, Jun. 2003, pp. 520-527.

(Continued)

*Primary Examiner* — Richard Isla Rodas
*Assistant Examiner* — Johali Torres Ruiz
(74) *Attorney, Agent, or Firm* — Foley & Lardner LLP (57) ABSTRACT

A case for an implantable medical device includes a metal case portion, having an inside and an outside, configured to attach to at least one other case portion to define a biocompatible case for the implantable medical device. The metal case portion has a plurality of grooves disposed on at least one of the inside and the outside, the grooves being oriented substantially perpendicular to an expected direction of eddy currents produced by an inductive recharging coil in proximity thereto.

19 Claims, 8 Drawing Sheets

(56) References Cited

U.S. PATENT DOCUMENTS

| | | | |
|---|---|---|---|
| 6,144,204 A * | 11/2000 | Sementchenko | G01R 33/385 |
| | | | 324/318 |
| 6,240,318 B1 | 5/2001 | Phillips | |
| 6,516,227 B1 | 2/2003 | Meadows et al. | |
| 6,972,543 B1 | 12/2005 | Wells | |
| 7,177,691 B2 | 2/2007 | Meadows et al. | |
| 7,268,410 B1 * | 9/2007 | Hopper | H02M 7/003 |
| | | | 257/379 |
| 7,295,878 B1 * | 11/2007 | Meadows | A61N 1/3787 |
| | | | 607/61 |
| 7,729,760 B2 | 6/2010 | Patel et al. | |
| 7,751,891 B2 | 7/2010 | Armstrong et al. | |
| 7,769,466 B2 | 8/2010 | Denker et al. | |
| 2001/0051317 A1 * | 12/2001 | Nakano | G03F 7/2059 |
| | | | 430/296 |
| 2004/0104370 A1 * | 6/2004 | Suzuki | F16K 31/0665 |
| | | | 251/129.15 |
| 2005/0075697 A1 | 4/2005 | Olson et al. | |
| 2005/0113888 A1 * | 5/2005 | Jimenez et al. | 607/61 |
| 2005/0113889 A1 * | 5/2005 | Jimenez et al. | 607/61 |
| 2005/0119716 A1 | 6/2005 | McClure et al. | |
| 2006/0247737 A1 | 11/2006 | Olson et al. | |
| 2007/0129767 A1 | 6/2007 | Wahlstrand | |
| 2009/0008029 A1 * | 1/2009 | Deininger | 156/247 |
| 2009/0082833 A1 * | 3/2009 | Wosmek | A61N 1/08 |
| | | | 607/60 |
| 2009/0096413 A1 * | 4/2009 | Partovi | H01F 5/003 |
| | | | 320/108 |
| 2009/0210035 A1 | 8/2009 | Gelbart | |
| 2010/0076524 A1 | 3/2010 | Forsberg et al. | |
| 2010/0106223 A1 | 4/2010 | Grevious et al. | |
| 2010/0114253 A1 | 5/2010 | Wahlstrand | |
| 2010/0137948 A1 | 6/2010 | Aghassian et al. | |
| 2010/0182116 A1 * | 7/2010 | Ishimoto et al. | 336/192 |
| 2010/0320843 A1 * | 12/2010 | Kitamura | H01F 27/34 |
| | | | 307/104 |
| 2011/0046699 A1 | 2/2011 | Mazanec | |
| 2011/0234155 A1 * | 9/2011 | Chen et al. | 320/108 |
| 2012/0262108 A1 | 10/2012 | Olson et al. | |

OTHER PUBLICATIONS

Sung-Noon Cho et al., "A Wireless Powered Fully Integrated SU-8-Based Implantable LC Transponder," Technical Paper, Microsyst Technol, Springer-Verlag 2010, Received Jul. 17, 2009, Accepted Feb. 16, 2010, Published Online, Mar. 9, 2010, 7 pages.
Gurhan Alper Kendir et al., "An Optimal Design Methodology for Inductive Power Link with Class-E Amplifier," IEEE Transactions on Circuits and Systems—I: Regular Papers, vol. 52, No. 5, May 2005, pp. 857-866.

* cited by examiner

INDUCTIVELY RECHARGEABLE IMPLANTABLE DEVICE WITH REDUCED EDDY CURRENTS

BACKGROUND

Field of the Disclosure

The present disclosure generally relates to rechargeable implantable electrical devices. More particularly, the present disclosure relates to an implantable device, with an inductive recharging system, having a metal case that is designed to reduce the effects of eddy currents during recharging.

Description of the Related Art

There are a variety of implantable devices for which it is desirable to provide inductive electrical recharging. Such devices can include pacemakers, implantable drug delivery systems and nerve stimulation devices. Among the latter are implantable devices for nerve stimulation, such as vagus nerve stimulation (VNS). VNS has been used as a treatment for intractable epilepsy. VNS is achieved through an implanted device, such as a pulse generator that delivers a bipolar, biphasic pulse to the vagus nerve. The implant procedure is very similar to the implantation of a pacemaker. The pulse generator is implanted subcutaneously, typically in the upper left chest wall. An electric lead is connected between the pulse generator and one or more electrodes on the vagus nerve using a subcutaneous tunneling tool to the left vagus nerve, which lies in the carotid sheath.

Many implantable devices were originally designed with non-rechargeable batteries. More recently, however, rechargeable devices have been developed, allowing a user to periodically recharge the device using an inductive recharger that is magnetically coupled with inductive recharging elements of the implanted device. Such recharging presents several challenges. In many implantable devices, the inductive recharging elements of the implanted device are located in the body of the device itself, which is often housed in a metal case, made of materials such as stainless steel or titanium. Unfortunately, the metal case can contribute to the formation of eddy currents during inductive recharging. These eddy currents waste energy (which lengthens the time required for recharging) and also cause heating of surrounding tissue, which is a significant issue.

It is desirable to provide safe, simple, and convenient recharging of implanted devices, while minimizing the production of eddy currents and undesirable heating of surrounding tissues. The present disclosure is directed to overcoming, or at least reducing the effects, of one or more of the issues set forth above.

SUMMARY

It has been recognized that it would be advantageous to develop a rechargeable implantable device that has reduced susceptibility to eddy current formation during inductive recharging.

In accordance with one aspect thereof, the present disclosure provides an implantable device, having an inductive recharging coil, coupled to a rechargeable battery and control circuitry, adapted to provide recharging current to the rechargeable battery in response to a proximate electromagnetic field. A conductive case, adapted for subcutaneous implantation, encases the rechargeable battery, the control circuitry and the inductive recharging coil. The conductive case has at least one of an inner surface and an outer surface with a pattern of grooves disposed thereupon, the grooves being oriented substantially normal to an anticipated direction of eddy current flow in response to the proximate electromagnetic field In accordance with another aspect thereof, the present disclosure provides a case for an implantable medical device. The case includes a metal case portion, having an inside and an outside, configured to attach to at least one other case portion to define a biocompatible case for the implantable medical device. The metal case portion has a plurality of grooves disposed on at least one of the inside and the outside, the grooves being oriented substantially perpendicular to an expected direction of eddy currents produced by an inductive recharging coil in proximity thereto.

In accordance with yet another aspect thereof, the disclosure provides a rechargeable, implantable system including an external recharging device, having a first inductive recharging coil, and an implantable device. The implantable device includes a rechargeable battery, a second inductive recharging coil, and a metal case housing the rechargeable battery and the second inductive recharging coil. The second inductive recharging coil is coupled to the rechargeable battery, and is configured to provide recharging current to the rechargeable battery in response to a proximate electromagnetic field of the first recharging coil. The metal case has a front face disposed between the first and second inductive recharging coils. The front face has a plurality of grooves disposed on at least one of an inside and an outside of the front face, the grooves being oriented substantially perpendicular to an expected direction of eddy currents produced by operational proximity of the first and second inductive recharging coils.

These and other embodiments of the present application will be discussed more fully in the description. The features, functions, and advantages can be achieved independently in various embodiments of the claimed invention, or may be combined in yet other embodiments.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope as defined by the appended claims.

DESCRIPTION OF ILLUSTRATIVE EMBODIMENTS

Illustrative embodiments are described below as they might be employed in a case for an implantable device, and a system employing the same. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments will become apparent from consideration of the following description and drawings. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

As used herein, the term "implantable" means a device that can be completely subcutaneously implanted into a human or animal body, with no portions of the apparatus extending outside the body after implantation.

As used herein, the term "implantable device" means any type of electrical device that is implantable into a human or animal body, and is configured to affect the function of the body. A device that affects the function of the body can also be called an active implantable medical device or simply an implantable medical device (IMD). Examples of implantable medical devices include cardiac pacemakers, nerve stimulation devices, and implantable drug delivery devices.

As used herein, the terms "high resistance metal case" and "high resistance titanium case" have reference to a metal case that has been modified in some way that increases its electrical resistance to eddy current formation in the presence of an oscillating electrical field. Such modifications can include the addition of surface features or characteristics on an inner and/or outer surface of the case, such as grooves, etching, surface texture, etc., or modifications to the cross-section of the metal, such as a laminated cross-section, or a thinner than normal cross-section of metal.

Figure 1:
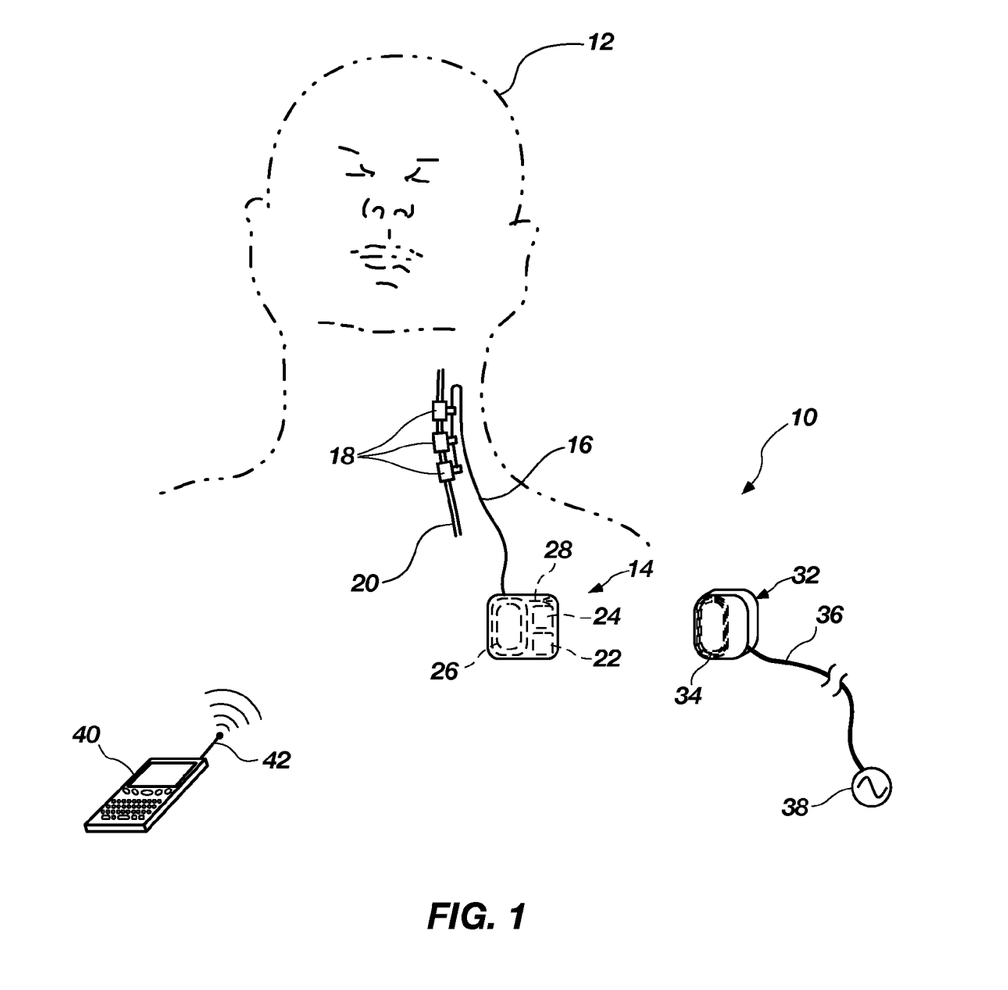
FIG. 1 is a schematic representation of a human subject showing a subcutaneous vagus nerve stimulation system, having a lead extending from an implantable device to electrodes attached at the left vagus nerve, and an external recharger.

As noted above, there are a variety of implantable devices for which it is desirable to provide remote communication and electrical recharging. Such devices include implantable devices for nerve stimulation, such as VNS. VNS was approved by the FDA in 1998 as an adjunctive therapy for epilepsy with partial onset seizures. Shown in FIG. 1 is a schematic diagram of one embodiment of an implantable vagus nerve stimulation system, indicated generally at 10, implanted into a patient 12. The system includes two main components: an implantable device 14, such as a pulse generator, and a tether or lead 16 that has one or more electrodes 18 at its distal end. The tether and electrodes are collectively referred to as the lead, and the lead provides an interface between the implantable device 14 and the electrodes 18. The electrodes 18 are attachable to the vagus nerve 20. An implantable VNS system of this type is commercially available, such as from Cyberonics, Inc. of Houston, Tex.

The implantable device 14 can be a multi-programmable device, which allows a physician to control several parameters. In one embodiment, the programmable parameters are signal amplitude (e.g. 0-3.5 mA), frequency (e.g. 1-30 Hz), pulse width (e.g. 130-1000 µs), signal ON time (e.g. 7-60 sec) and signal OFF time (e.g. 0.2-180 min). It is to be appreciated that these pulse parameters are only exemplary, and that other parameters and ranges can be used. The pulses can be delivered at the specified amplitude and frequency over the course of the ON time, and then during the OFF time, no stimulation takes place. In one embodiment, pulse settings can be 2 mA, at 25 Hz frequency, 250 µs pulse width, with a 30 sec ON time, and 5 min OFF time. The variability in parameters allows for the physician to adjust for greater efficacy or less severe side effects, depending on the patient.

The implantable VNS system 10 includes additional elements for recharging and communication. As shown in FIG. 1, the implantable device 14 includes a rechargeable battery 22, control circuitry 24, a secondary recharging coil 26 coupled to the rechargeable battery 22 and control circuitry, and an antenna 28. The rechargeable battery 22 and secondary recharging coil 26 are adapted to provide recharging current to the rechargeable battery 22 in response to a proximate electrical field. Specifically, these elements operate in conjunction with an external recharger 32, which also includes a primary recharging coil 34 and a connection 36 to a source of electrical power 38. In order to recharge the rechargeable battery 22 of the implantable device 14, the external recharger 32 is placed in a location so that the primary recharging coil 34 of the external recharger 32 is as near as possible to the secondary recharging coil 26 of the implantable device 14, so that the two coils become electro-magnetically linked through inductive coupling. The external recharger 32 can include an indicator light or other device (not shown) that gives feedback to indicate when the electro-magnetic charging link has been made, and to indicate the progress of recharging, such as to indicate when charging is complete.

When an alternating electric current is supplied to the primary recharging coil 34 of the external recharger 32, the electric field that is created induces an electrical current in the secondary recharging coil 26 of the implantable device 14, without any mechanical connection or direct contact between the two devices. The two coils become electro-magnetically linked through inductive coupling, allowing power to flow from one to the other. In this way, the external recharger 32, which is outside the body, can recharge the rechargeable battery 22 of the implantable device 14, which is inside the body.

The antenna 28 of the implantable device 14 can be configured to receive programming and control instructions from an external communications device 40 that also has an antenna 42. Programming and control instructions can be transmitted to circuitry (not shown) of the implantable device 14 from the communications device 40, and these are received by the antenna 28. Likewise, data regarding operation of the implantable device 14 can also be transmitted to the communications device 40 in a similar manner. The implantable device 14 may be programmed and/or controlled via wireless communication using the Medical Information Communication System (MICS), which uses radio waves transmit information to and from implantable device 14. A communicating ancillary device having an antenna (not shown) can also be provided for communication with the implantable device 14.

Figure 2A:
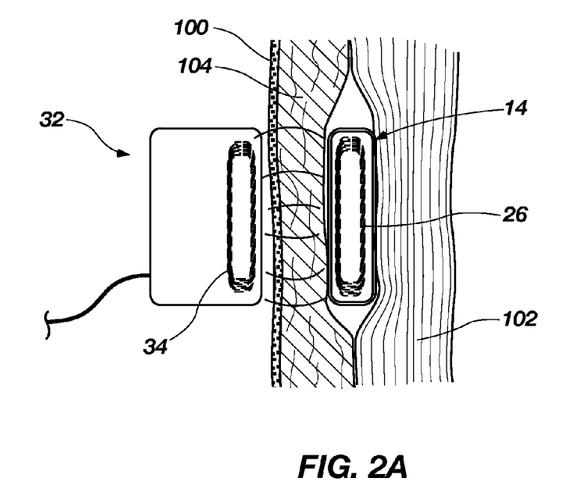
FIG. 2A is a cross-sectional view of an implantable device implanted subcutaneously, showing a secondary recharging coil of the implantable device, with an external recharger having a primary recharging coil positioned outside the body, showing flux lines extending between the external recharger and the secondary recharging coil of the implantable device.
Figure 2B:
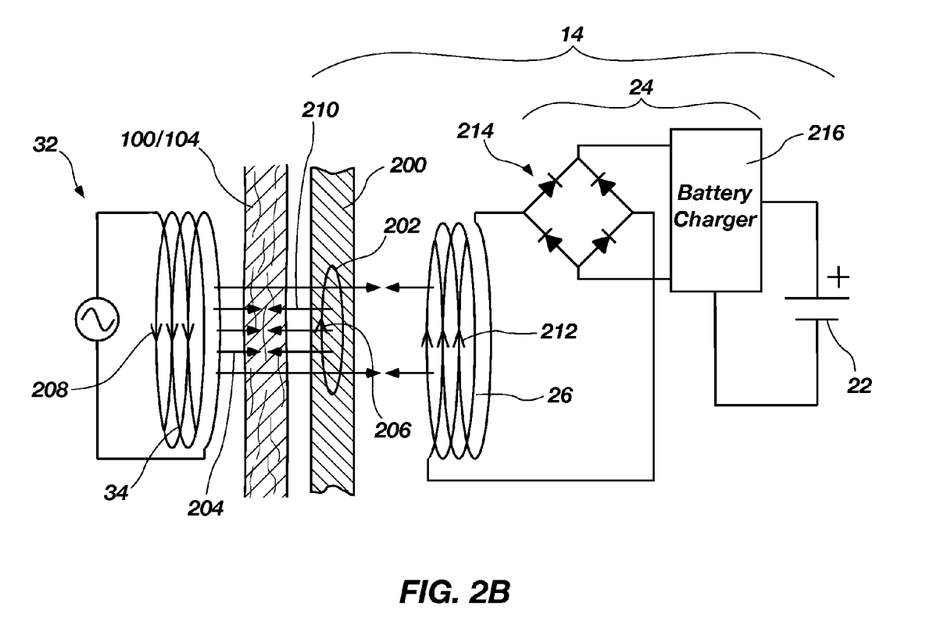
FIG. 2B is a schematic diagram of the recharging portions of an implanted device inductively linked with an external recharger, illustrating how eddy currents are formed in the case of the implantable device.

As noted above, in many rechargeable implantable devices, the inductive recharging elements of the implanted device are located in the body of the device itself, such as the implantable device 14 of the VNS system 10 shown in FIG. 1. The depth of implantation of the device affects charging time and power usage because the casing of the implanted device (e.g., titanium) and soft tissue between the device and the recharger can have the effect of attenuating power transfer between induction coils. A cross-sectional view of the implantable device 14 implanted in a body and an external recharger 32 are shown in FIG. 2A. A schematic diagram of the same is shown in FIG. 2B. The external recharger 32 is positioned nearby, illustrating a typical recharging operation.

In the view of FIG. 2A, a common aspect of implantable devices is illustrated. The implantable device 14 is implanted relatively deeply below the skin 100 and above deeper structures, such as underlying muscle 102, with a relatively large thickness of subcutaneous tissue 104 between the implantable device 14 and the skin 100. Relatively deep implantation of the implantable device 14 is desirable for comfort of the patient and protection of the controller device itself.

For efficient recharging, it is desirable that the secondary recharging coil 26 of the implantable device 14 be properly aligned with the primary recharging coil 34 of the external recharger 32—for example, directly over the implantable device 14. Rechargeable batteries can take 2-3 hours to recharge. Movement of the patient and variations in a patient's anatomy can contribute to poor alignment of the primary recharging coil 34 of the external recharger 32 with the secondary recharging coil 26 of the implantable device 14. Poor alignment of the primary recharging coil 34 and the secondary recharging coil 26 during recharging can extend the time needed for recharging.

Other factors that affect recharging are illustrated in FIG. 2B. One of these effects is the potential creation of eddy currents during recharging. The implantable device 14 shown herein has a metal case which contains the rechargeable battery 22, control circuitry 24, and the secondary recharging coil 26. The front portion of the metal case is indicated symbolically at 200. As used herein, the terms "front side" or "front portion" have reference to the portion of the metal case that faces outward from the patient, and lies between the induction coils during inductive recharging. In one embodiment, the outer case is of titanium or a titanium alloy, which is often used in medical applications because it is biologically inert and relatively resistant to degradation in the body. Other metal materials can also be used for this type of device, such as stainless steel, etc.

During recharging, with the primary recharging coil 34 of the external recharger 32 electromagnetically linked with the secondary recharging coil 26 of the implantable device 14, eddy currents, indicated at 202, can form in the metal case 200. Current in the primary recharging coil 34 generates a perpendicular magnetic field (B-field) 204, which propagates to the secondary recharging coil 26 of the implantable device 14. Because the front wall 200 of the metal case lies between the two induction coils, some portion of the electric flux between the two coils is drawn off and creates eddy currents 202 in the front wall 200 of the metal case. These eddy currents waste energy, which lengthens the time required for recharging. Specifically, the eddy currents in the case flow in the opposite direction, indicated by arrow 206 as the current in the primary recharging coil 34, as indicated by arrows 208, and generate an opposing B-field 210 that cancels out some of the B-field 204 from the primary recharging coil 34, thus opposing the transfer of electrical power to the secondary recharging coil 26 (in the implantable device 14). These eddy currents also directly produce heat in the front wall 200 of the metal case. Heating of the metal may cause damage to the surrounding tissue 100/104 when temperatures increase more than about 4° C. from normal.

The remaining primary B-field 204 that is not cancelled out by the opposing B-field 210, generated by the eddy currents 206, makes it to the secondary recharging coil 26 where a current is induced. This current is also flowing in the opposite direction of that in the primary recharging coil 34, as indicated by arrows 212. To recharge the rechargeable battery 22 of the implanted device, the current that is induced in the secondary recharging coil 26 is passed through an AC-DC rectifier 214. The rectified energy is passed into a battery charger circuit 216, where a constant current (e.g. 100 mA) can be fed into the rechargeable battery 22 until a desired voltage (e.g. 4.1 V) is reached. From that point, trickle charging of the rechargeable battery 22 at that constant voltage can be accomplished until the current drops below some lower threshold (e.g. 10 mA). The rectifier circuit 214 and battery charger circuit 216 can both be part of the general control circuitry 24 of the implanted device.

Figure 3:
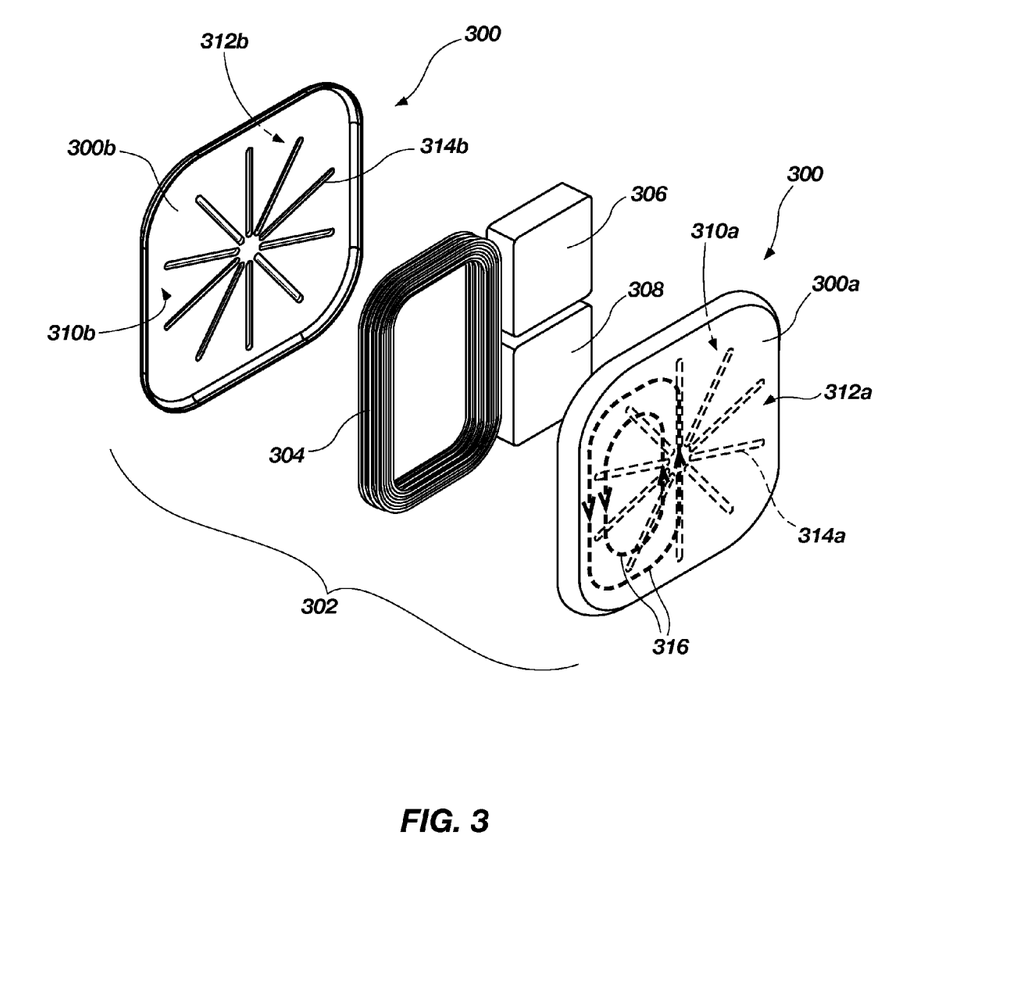
FIG. 3 is an exploded perspective view of an embodiment of an implantable device, wherein the metal case includes grooves on the inside of both the front and back portions of the case.
Figure 4A:
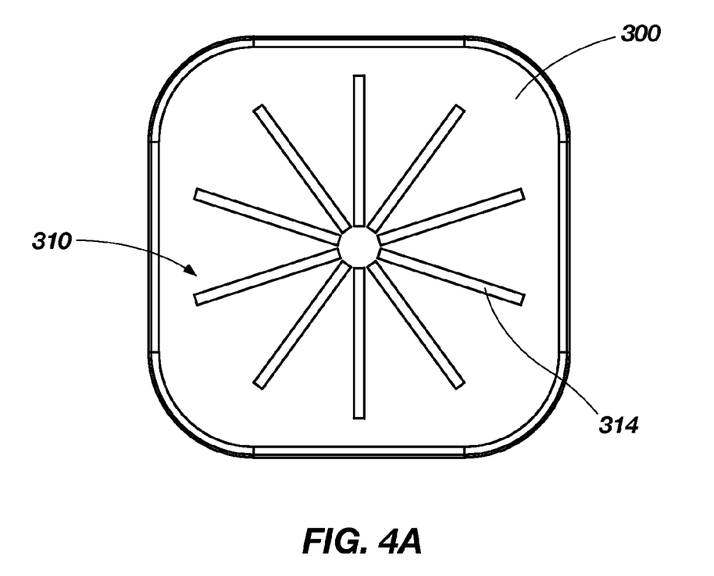
FIG. 4A is a plan view of the inside of one half of an embodiment of a metal case of an implantable device, having a radial pattern of grooves formed in a region of likely eddy current formation.

In order to address some of the effects associated with induced eddy currents, various configurations of a metal case for a rechargeable implanted device may be used to help reduce eddy current formation during inductive recharging. Shown in FIG. 3 is an exploded view of one embodiment of a metal case, indicated generally at 300, for an implantable device 302 having high resistance to eddy current formation. The implantable device 302 includes a front case portion 300a and a back case portion 300b, which are configured to attach to each other to define a biocompatible and sealed enclosure containing the inductive recharging coil 304, control circuitry 306 and rechargeable battery 308. As discussed above with respect to FIG. 1, the implantable device 302 can also include an antenna (not shown), which can be included as part of the control circuitry 306. The inductive recharging coil 304 is adapted to provide recharging current to the rechargeable battery 308 in response to a proximate electrical field. A plan view of one half of the metal case 300 is shown in FIG. 4A.

The front and back portions 300a, 300b of the metal case 300 each have an inside surface 310a, 310b, and an outside surface 312a, 312b. Advantageously, the front case portion 300a can include a pattern of grooves 314a, formed on the inside surface 310a, in a region of likely eddy current formation. These grooves are channels that are machined or otherwise formed in the inside surface and/or outside surface of the metal case 300. During inductive recharging, the proximate electrical fields related to the inductive recharging coil 304 are likely to induce eddy currents, indicated by current flow lines 316, which circulate in the metal case 300. Advantageously, the grooves 314a provide resistance to the flow of these eddy currents, thus making the metal case 300 a high resistance metal case. The grooves can be oriented substantially perpendicular to a direction of expected eddy current flux in the metal case 300. An anticipated direction of eddy current flow is shown by the current flow lines 316 in FIG. 3, and it can be seen that at least some of the grooves 314a are substantially perpendicular to the flow direction. A groove that is oriented substantially perpendicular to a direction of eddy current flow will resist the eddy current by providing a barrier of higher electrical resistance in the flow path. The thinner material of the case in the bottom of the groove provides this higher resistance, and the orientation of the groove perpendicular to the eddy current flow path effectively cuts off alternate pathways for the eddy current flow.

Figure 4B:
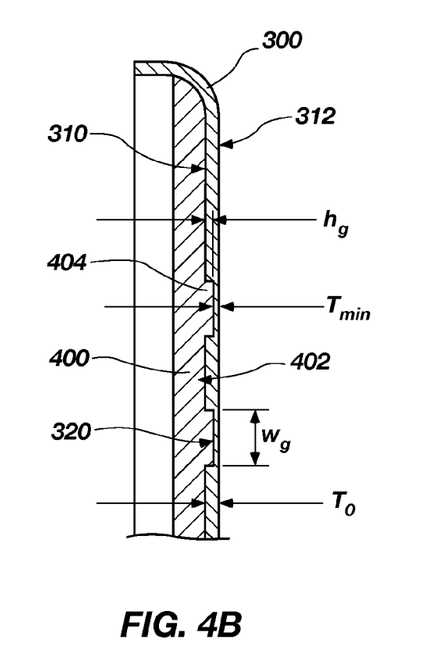
FIG. 4B is a partial cross-sectional view of a portion of the metal case of FIG. 4A, showing the configuration of the grooves, and showing in cross-section a polymer insert that nests within the grooves.

As shown in FIG. 4B, these grooves have a width $w_g$ and a depth $h_g$. The depth $h_g$ of the groove, subtracted from the overall thickness of the case $T_0$ leaves a remaining case thickness in the bottom of the groove of $T_{min}$. As noted above, the reduced thickness $T_{min}$ of the metal case 300 in the bottom 320 of the groove provides increased resistance to current flow, compared to the total or nominal thickness $T_0$ of the case, and therefore resists eddy current flow. The width and depth of the grooves can vary. To provide good resistance to eddy current flow, it has been found to be generally desirable that the grooves have vertical sides and a flat bottom, relative to the surface of the metal case 300. In one embodiment, the grooves have a width $w_g$ of about 1 to 2 mm, and a depth $h_g$ of about 0.2 mm in a case having a nominal thickness $T_0$ of 0.3 mm. Other sizes can also be used. It is generally believed that deeper grooves are better at reducing eddy currents, and that as grooves become wider, their effectiveness decreases. Naturally, however, both of these considerations have limits with respect to practicality and their effect on the structural strength of the metal case 300.

More broadly, it is believed that grooves having a width $w_g$ of from 0.1 mm to 6.5 mm and a groove depth $h_g$ of 0.1 mm to 0.2 mm can be effectively used with a titanium case having an overall thickness $T_0$ of 0.3 mm. This leaves a remaining case thickness $T_{min}$ of 0.1 mm to 0.2 mm between the bottom of the groove 320 and the outside surface 312 of the case. Cases having a different nominal thickness can also be used, and those of skill in the art will recognize that the nominal thickness for a metal case will depend on the properties of the material. For titanium, it is believed that cases having a nominal thickness $T_0$ of 0.1 mm to 0.9 mm can be used. For stainless steel, a thickness $T_0$ of approximately 0.3 mm is believed to be acceptable, and grooves having a width $w_g$ of from 0.1 mm to 6.5 mm and a groove depth $h_g$ of 0.1 mm to 0.2 mm can be effectively used.

Figure 5A:
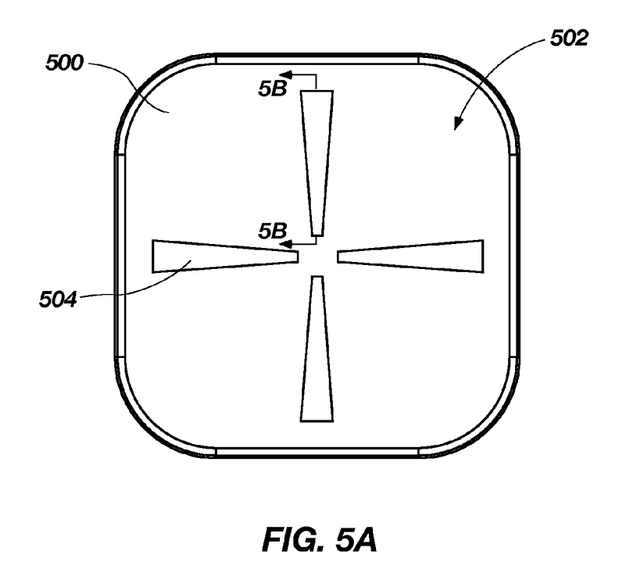
FIG. 5A is a plan view of the inside of one half of another embodiment of a metal case of an implantable device, having a cross-shaped pattern of grooves formed in a region of likely eddy current formation, the grooves having a tapering width.
Figure 5B:
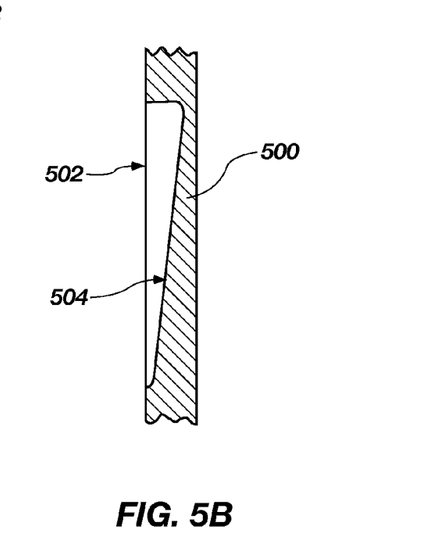
FIG. 5B is an enlarged, partial cross-sectional view taken longitudinally through one groove of the embodiment of FIG. 5A, showing the tapered depth of the groove.
Figure 6:
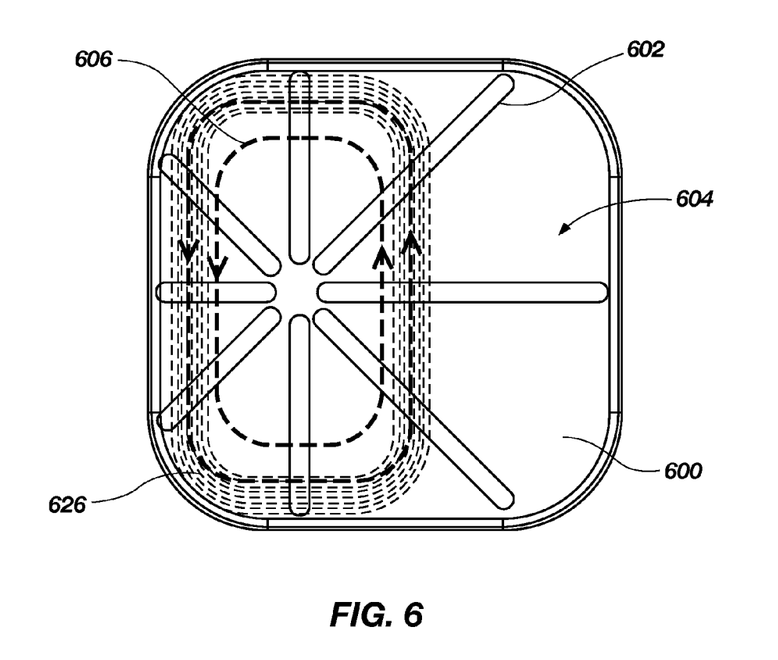
FIG. 6 is a plan view of the inside of one half of another embodiment of a metal case of an implantable device, having a radial pattern of grooves that are positioned off-center on the surface of the case.
Figure 7A:
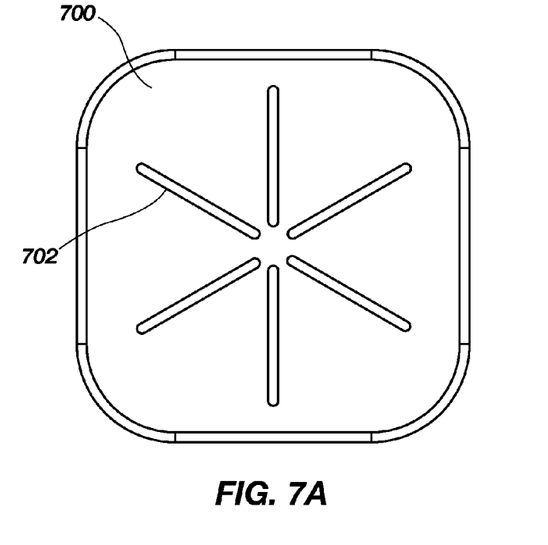
FIG. 7A is a plan view of the inside of one half of another embodiment of a metal case of an implantable device, having a radial pattern of grooves that extend entirely through the cross-section of the case, with a dielectric filler material in the grooves.

A variety of groove patterns can be used to resist eddy currents. In the embodiment of FIG. 3 and FIG. 4A, the grooves 314 are arranged in a radial pattern having ten spokes, the pattern being substantially centered in the case 500. In the embodiment of FIG. 5A, the inside surface 502 of the case 500 includes a radial pattern of four grooves 504 arranged in a cross pattern. In the embodiment of FIG. 6, a radial pattern of eight grooves 602 is shown. In the embodiment of FIG. 7A, a radial pattern of six grooves 702 is shown. The end condition of the grooves can also vary. For example, in the embodiments of FIGS. 3, 6 and 7, the ends of the grooves are rounded. In the embodiments of FIGS. 4A and 5, the ends of the grooves are substantially square. In addition, the width and/or depth of the grooves may be non-uniform. For example, in the radial pattern shown in FIG. 5A, the width of the grooves 504 near the center of the radial pattern is less than the width of the grooves near the outside edge of the radial pattern such that the width of the grooves is tapered. Also, the depth of the grooves may be non-uniform. For example, as shown in the partial cross-sectional view of FIG. 5B, the depth of the grooves 504 near the center of the radial pattern in this embodiment is less than the depth of the grooves near the outside edge of the radial pattern such that the depth of the grooves is tapered. Tapering the width and/or depth of the grooves may provide greater mechanical strength and support at the center of the radial pattern where the case may be weak as a result of the grooves being close together. Additional types of radial patterns may be used as well as a variety of other patterns, combinations of patterns, groove types, and combinations of groove types. For example, the radial groove patterns that are shown herein are non-collinear patterns because the grooves are not substantially parallel to each other. However, it is to be appreciated that collinear or parallel groove patterns as well as other non-collinear patterns can also be used.

Figure 10:
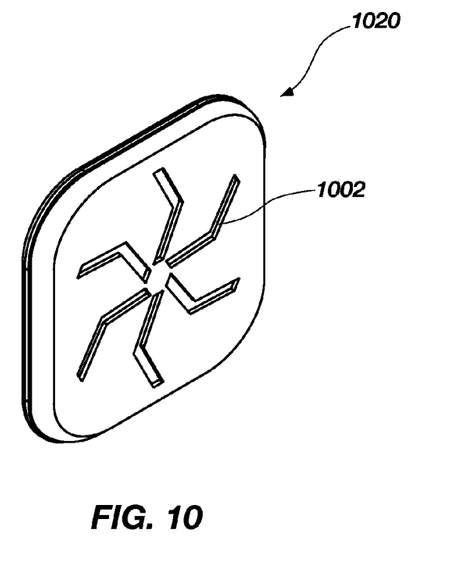
FIG. 10 is a perspective view of an embodiment of an implantable device wherein the outside surface of the front portion of the case includes a pattern of angled grooves.
Figure 11:
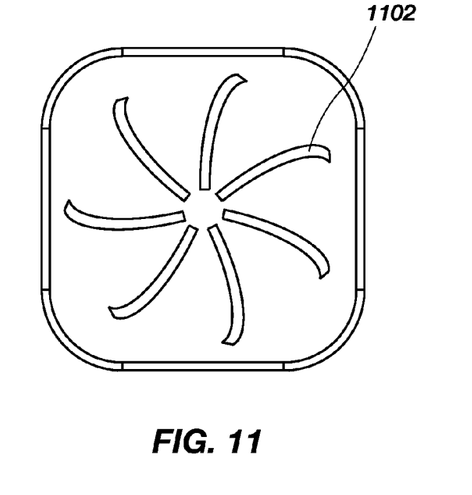
FIG. 11 is a plan view of one half of another embodiment of a metal case of an implantable device, having a pattern of curved grooves.

In other embodiments, the grooves may be non-linear (e.g., curved, angled, jagged). For example, shown in FIG. 10 is a radial pattern of grooves 1002 having an angle in them, arranged in a radial pattern. Shown in FIG. 11 is a radial pattern of grooves 1102 having curved side edges.

Figure 12:
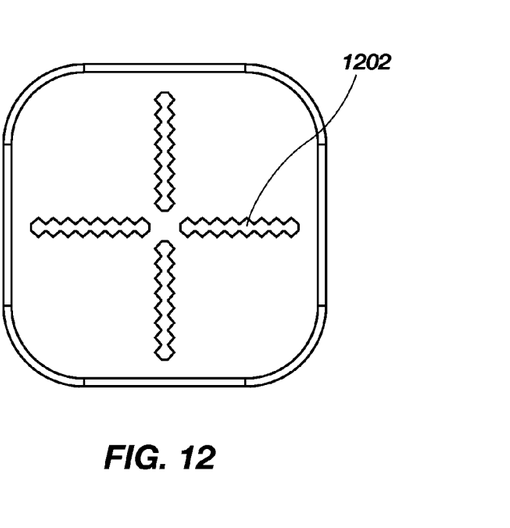
FIG. 12 is a plan view of one half of another embodiment of a metal case of an implantable device, having a pattern of grooves with jagged edges.
Figure 13A:
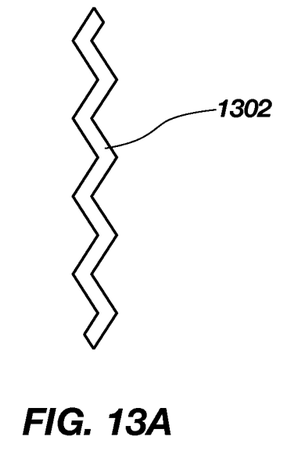
FIGS. 13A-C are plan views of other embodiments of grooves having angles, jagged grooves, and grooves with curved edges, respectively.
Figure 13B:
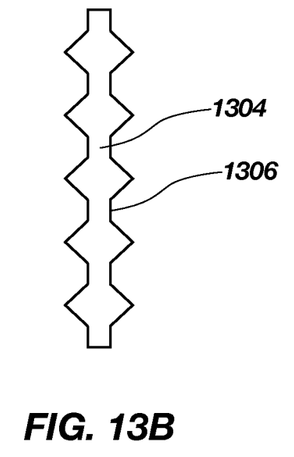
Figure 13C:
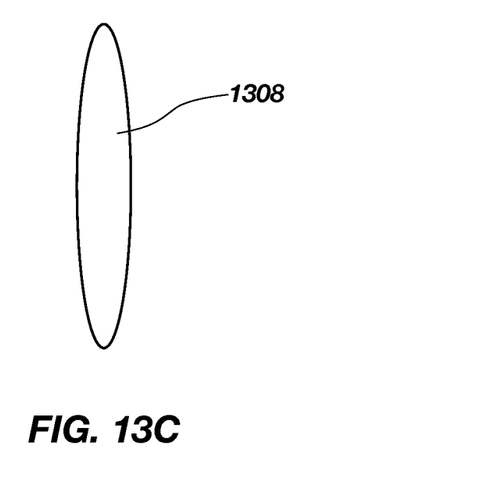

Shown in FIG. 12 is a cross-type pattern of grooves 1202 having jagged edges. Additional groove patterns are shown in FIGS. 13A-C. For example, shown in FIG. 13A is another embodiment of a groove 1302 having angles. Unlike the grooves 1002 of FIG. 10, which include only one angle, the groove 1302 of FIG. 13A includes multiple angles, providing a generally zig-zag shape. Another groove 1304 having jagged edges is shown in FIG. 13B. This groove pattern is similar to the jagged groove 1202 of FIG. 12, but includes parallel side wall sections 1306 between adjacent jagged portions. Finally, another embodiment of a groove 1308 having curved side edges is shown in FIG. 13C. Whereas the curved grooves 1102 of FIG. 11 have parallel side edges, the groove 1308 of FIG. 13C has side edges that curve away from each other, in a generally elliptical shape.

The location and orientation of the grooves can also vary. Referring to FIG. 6, where eddy currents 606 are expected to flow in a given area of the metal case 600, the grooves 602 formed on the inside surface 604 of the metal case 600 can be centered upon the region of eddy current flow, rather than being symmetrical with respect to the case itself. In the embodiment of FIG. 6, the grooves 602 are arranged in a radial pattern that is positioned off-center with respect to the surface of the metal case 600, but is centered at an approximate center of the expected eddy current flow path 606. This configuration is useful where, as shown, the inductive recharging coil 626 in the implantable device is positioned off-center with respect to the entire implantable device. In this case, the center of the radial pattern of grooves is positioned over the center of likely eddy current formation, which is off-center with respect to the case of the implantable device. With this configuration, the grooves are oriented substantially perpendicular to the expected flow path of the eddy currents throughout that flow path. This helps to reduce those eddy currents. Similar centering of the groove pattern in the region of likely eddy current formation can be used with the other groove patterns shown and described herein.

It is to be understood that the shape, size, position, pattern, width, depth and any other feature of grooves shown herein can be varied in any combination of the ways disclosed herein in any given case. That is, any combination of shape, placement, size, etc. of the grooves can be used in any particular embodiment, in accordance with this disclosure, and this disclosure is not limited to the specific combinations shown herein. Any shape of grooves can have a tapered width or depth. Any pattern of grooves can include grooves of any shape and be placed in any location, on the inside or outside of the case.

Other features and characteristics can also be associated with the grooves in the metal case. Shown in cross-section in FIG. 4B is a non-conductive layer 400 provided over the grooves 314. The non-conductive layer 400 may be any type of dielectric and/or electromagnetically transparent material. The non-conductive layer 400 may be a polymer, ceramic, carbon fiber, or any other suitable composite material. The non-conductive layer 400 may be deposited, grown, molded, or otherwise applied over the grooves 314. In one embodiment, the non-conductive layer may be a polymer insert that may be attached to the inner surface 310 of the metal case half 300, and has a front side 402 with ridges 404 shaped and positioned to nest in the grooves 314 shown in FIG. 4A. The polymer insert may be directly molded to the case or attached using fasteners or adhesive. The polymer insert may be of polypropylene or other durable non-conductive material. The polymer insert provides additional strength to the case, as well as a smooth interior surface for the case. In another embodiment, grooves formed on the exterior of the case, as shown in FIG. 10, may be covered by an exterior non-conductive layer. The exterior non-conductive layer may be a biocompatible polymer or ceramic. The biocompatible polymers may include Polysulfone, PEEK (polyether ether ketone), and Urethanes.

Figure 7B:
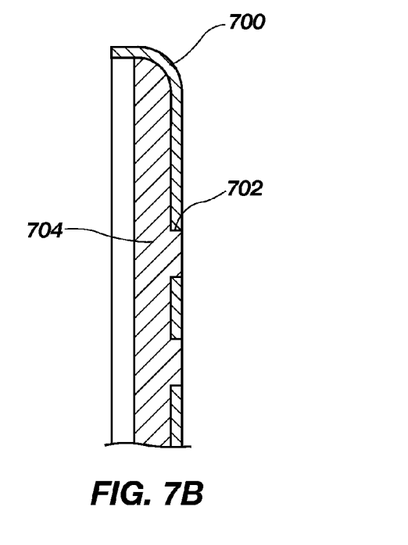
FIG. 7B is a partial cross-sectional view of a portion of the metal case of FIG. 7A, showing the configuration of the grooves, and showing in cross-section the dielectric filler material.

As noted above, deeper grooves tend to be more effective at reducing eddy currents. Shown in FIG. 7A is a plan view of a metal case 700 for an implantable pulse generation device, having a radial pattern of grooves 702 that extend entirely through the cross-section of the metal case 700. That is, the grooves are through slots, and are filled with a filler material 704 to seal the metal case 700 as shown in FIG. 7B. The filler material 704 may be part of a polymer insert, a ceramic material, or any other biocompatible material having a higher resistance to the formation and flow of eddy currents than the metal forming the metal case 700. FIG. 7B is a cross-sectional view of a portion of the metal case 700 of FIG. 7A, showing the configuration of the grooves 702, and showing in cross-section the dielectric filler material 704. It has been found that grooves that extend entirely through the thickness of the metal case 700 are very effective at reducing eddy current flow by entirely interrupting the electrical conductor at one or more locations along the eddy current flow path. Thus, where a groove that is generally perpendicular to eddy current flow helps reduce that flow by presenting electrical resistance, a slot that entirely removes the metal conductor and replaces it with a dielectric material has an even greater effect.

Grooves that are generally perpendicular to eddy current flow may help reduce eddy currents because the thickness of material across the bottom of the groove is substantially reduced. This thinner cross-section of material presents increased resistance to eddy current flow, and thereby reduces the eddy currents. Applying this concept more generally, it has been found that significantly reducing the overall cross-sectional thickness of the metal case in a region of likely eddy current formation also helps reduce eddy currents.

Figure 8A:
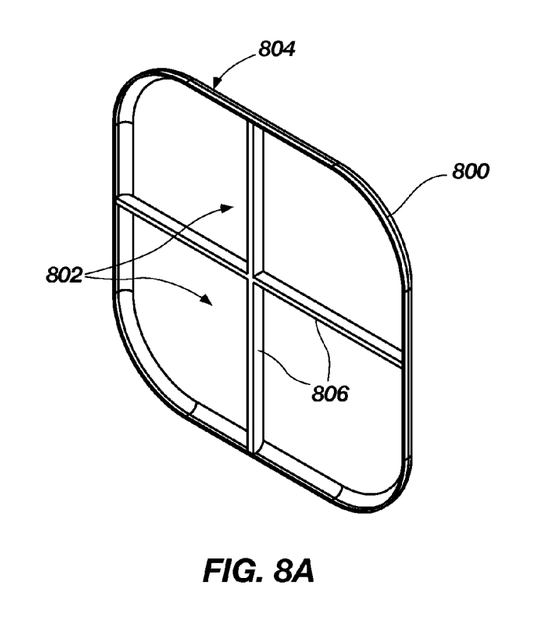
FIG. 8A is a perspective view of another embodiment of a metal case of an implantable device having a thin cross-section and stiffening ribs.
Figure 8B:
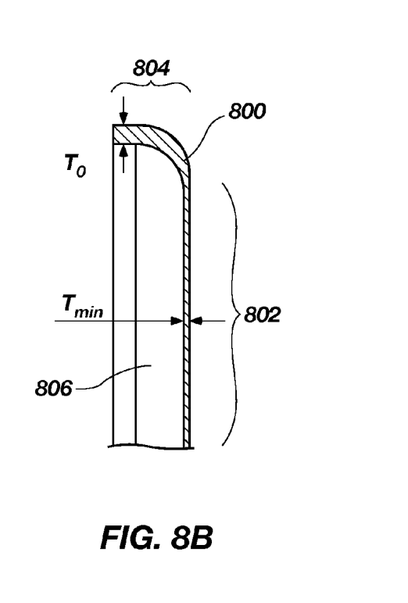
FIG. 8B is a close-up, partial cross-sectional view of the embodiment of FIG. 8A, showing the relative thickness of the case wall.

Shown in FIG. 8A is a perspective view of one half 800 of an embodiment of a metal case of an implantable pulse generation device having a thin cross-section. FIG. 8B is a close-up, partial cross-sectional view of the embodiment of FIG. 8A, showing the relative thickness of the case wall. In this embodiment, the metal case has relatively high thickness in areas where greater structural strength is desired, but has a significantly reduced cross-sectional thickness in areas of likely eddy current formation. As noted above, it has been found that thinner metal provides greater resistance to eddy current flow. Consequently, in the embodiment of FIGS. 8A and 8B, the high resistance metal case 800 has a reduced cross-sectional thickness $T_{min}$ in the side wall area 802 (the area of most likely eddy current formation), and a greater cross-sectional thickness $T_0$ in the edge region 804, where greater structural strength is desired for the connection to the other half of the case. In one embodiment the reduced cross-sectional thickness $T_{min}$ is less than about 0.3 mm in the side wall area 802, while the greater thickness $T_0$ is about 0.35 mm in the edge region 804, where one case half joins to the other. With such a thin case wall, stiffening ribs 806 can be provided to give additional strength to the wall.

Grooves for resisting eddy currents can be provided on the inner surface of only the front side of the metal case. For example, viewing FIG. 3, the grooves 314a can be disposed only on an inner surface 310a of the front side or half 300a of the metal case 300. However, grooves 314b can also be provided on the inner surface 310b of the back side 300b of the metal case, as shown in FIG. 3. In this embodiment the metal case includes grooves on the inside of both the front and back portions 300a, 300b of the case 302. While grooves can be provided on the front and back portions of the metal case, it is believed that the grooves 314a on the front side 300a of the case provide most of the eddy current reducing effect.

Figure 9:
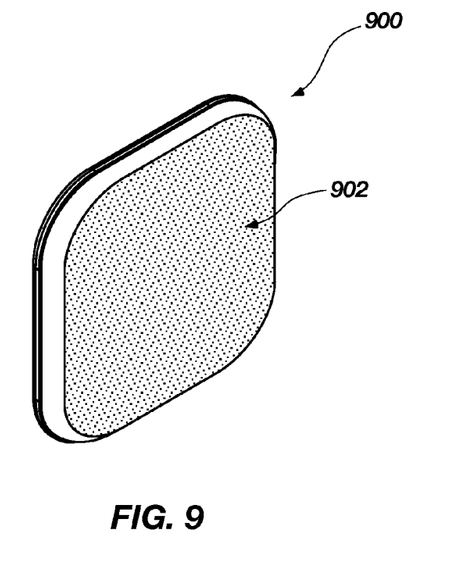
FIG. 9 is a perspective view of an embodiment of an implantable device wherein the outside surface of the front portion of the case has been roughened.

It has been found that eddy currents can also be reduced by providing a roughened texture or surface on the inside and/or the outside of the metal case of the implantable device. The roughened texture may be formed according to a pattern (e.g., selectively textured) or in a randomized fashion. Shown in FIG. 9 is a perspective view of an embodiment of an implantable pulse generation device 900 wherein the outside surface 902 of the front portion of the case has been roughened. This can be done by sandblasting, etching or other processes to increase surface roughness. In some embodiments, the roughened texture may be used in combination with the grooves to reduce eddy currents in the metal case.

As noted above, grooves can also be provided on an outside surface of the implantable device. For example, as shown in FIG. 10, an implantable pulse generation device 1020 includes a pattern of grooves 1002 on the outside surface of the front portion of the case. In the embodiment shown in FIG. 10 these grooves are angled, but any pattern, position or number of grooves can be used, as discussed herein.

The embodiments shown herein thus provide a metal case for an implantable device that has been modified to increase its resistance to eddy current formation during inductive recharging. In general, grooves on an inside and/or outside of a metal case of an implantable device that are positioned to be substantially perpendicular to an anticipated eddy current flow can effectively reduce eddy current formation. Where eddy currents flow in a generally circular pattern, a radial pattern of grooves has been found effective, and this radial pattern can take many forms. In one embodiment, the grooves extend entirely through the cross-section, and are filled with a dielectric material which seals the case. In yet another approach, the case wall can have a substantially reduced thickness. Alternatively, the inside and/or outside of the metal case can be roughened to reduce eddy currents.

Although various embodiments have been shown and described, the invention is not so limited and will be understood to include all such modifications and variations as would be apparent to one skilled in the art. For example, equivalent elements may be substituted for those specifically shown and described, certain features may be used independently of other features, and the number and configuration of various components described above may be altered, all without departing from the spirit or scope of the invention as defined in the appended claims.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. An implantable device, comprising:
a conductive case, adapted for subcutaneous implantation, encasing a rechargeable battery, a control circuitry, and an inductive recharging coil, the inductive recharging coil, coupled to the rechargeable battery and the control circuitry, adapted to provide recharging current to the rechargeable battery in response to a proximate electromagnetic field, the conductive case including an outer shell, the outer shell having an outer surface with a pattern of grooves disposed thereupon, the grooves being oriented substantially normal to an anticipated direction of eddy current flow in response to the proximate electromagnetic field generated by the inductive recharging coil wherein the inductive recharging coil is not attached to a magnetic shield;
wherein the grooves are arranged in a substantially radial pattern on the outer surface of the outer shell;
wherein a depth of at least one groove of the pattern of grooves is non-uniform along a radial length of the groove.

2. The device in accordance with claim 1, wherein a width of at least one groove of the pattern of grooves is non-uniform.

3. The device in accordance with claim 1, wherein the radial pattern is centered at an approximate center of an expected eddy current generation where the approximate center of the expected eddy current generation is not aligned with a center of the outer shell.

4. The device in accordance with claim 1, wherein the grooves other than a non-uniform groove have a width of about 1 to 2 mm, and a groove depth of about 0.15 mm.

5. The device in accordance with claim 1, wherein the grooves extend entirely through the conductive case, and further comprising a dielectric material disposed on the grooves.

6. The device in accordance with claim 1, wherein the conductive case comprises a front side, and the grooves are disposed on a front side outer surface.

7. The device in accordance with claim 1, further comprising a polymer insert, attached to an inner surface of the conductive case, having a front surface shaped to nest in the grooves.

8. The device in accordance with claim 1, wherein the conductive case has a minimum cross-sectional thickness that is less than about 0.5 mm.

9. The device in accordance with claim 1, wherein the conductive case includes at least one of an interior surface and an exterior surface having a roughened texture.

10. The device in accordance with claim 1, wherein a groove surface comprises a roughened texture.

11. A case for an implantable medical device, comprising a metal case portion, the metal case portion encasing a rechargeable battery, a control circuitry and an inductive recharging coil, the metal case portion forming an outer shell, the outer shell having an inside surface and an outside surface, configured to attach to at least one other case portion to define a biocompatible case for the implantable medical device, the metal case portion which formed the outer shell having a plurality of grooves disposed on the outside surface, the grooves being oriented substantially perpendicular to an expected direction of eddy currents produced by the inductive recharging coil in proximity thereto wherein the inductive recharging coil is not attached to a magnetic shield;
wherein the grooves are arranged in a substantially radial pattern on the outside surface;
wherein a depth of at least one groove of the plurality of grooves is non-uniform along a radial length of the groove.

12. The case for an implantable medical device in accordance with claim 11, wherein the substantially radial pattern is centered upon an expected center of eddy current generation.

13. The case for an implantable medical device in accordance with claim 12, wherein the grooves extend entirely through the metal case portion, and further comprising a dielectric material disposed on the grooves.

14. The case for an implantable medical device in accordance with claim 11, wherein the metal case portion comprises titanium or titanium alloy, having a minimum thickness that is less than about 0.5 mm.

15. A rechargeable, implantable system, comprising:
an external recharging device, having a first inductive recharging coil; and
an implantable device having:
a rechargeable battery;
a second inductive recharging coil, coupled to the rechargeable battery, and configured to provide recharging current to the rechargeable battery in response to a proximate electromagnetic field of the first recharging coil; and
a metal case housing the rechargeable battery and the second inductive recharging coil, the metal case having an outer shell, the outer shell including a front face, the metal case having the front face disposed between the first inductive recharging coil and the second inductive recharging coil, the front face having a plurality of grooves disposed on an outside of the front face, the grooves being oriented substantially perpendicular to an expected direction of eddy currents produced by operational proximity of the first inductive recharging coil and the second inductive recharging coil;
wherein the grooves are arranged in a substantially radial pattern on the outside of the front face;
wherein a depth of at least one groove of the plurality of grooves is non-uniform along a radial length of the groove.

16. The system in accordance with claim 15, wherein the substantially radial pattern is centered upon an expected center of eddy current generation.

17. The system in accordance with claim 16, wherein the plurality of grooves extend through the front face of the metal case, and further comprising a dielectric material disposed on the grooves.

18. The system in accordance with claim 15, wherein the metal case comprises titanium and has a minimum thickness of less than about 0.5 mm.

19. The system in accordance with claim 16, further comprising a roughened surface on at least one of an exterior surface and an interior surface of the front face.

* * * * *